(12) United States Patent
Lesage

(10) Patent No.: US 6,170,714 B1
(45) Date of Patent: Jan. 9, 2001

(54) DEVICE FOR DISPENSING EXTRUDABLE MATERIAL, SUCH AS A PASTE FOR DENTAL USE

(76) Inventor: Patrick Lesage, 9 rue Constantine, 35400 Saint Malo (FR)

( * ) Notice: Under 35 U.S.C. 154(b), the term of this patent shall be extended for 0 days.

(21) Appl. No.: 09/319,278

(22) PCT Filed: Dec. 23, 1997

(86) PCT No.: PCT/FR97/02391

§ 371 Date: Jun. 15, 1999

§ 102(e) Date: Jun. 15, 1999

(87) PCT Pub. No.: WO98/28090

PCT Pub. Date: Jul. 2, 1998

(30) Foreign Application Priority Data

Dec. 23, 1996 (FR) .................................................. 96 15847

(51) Int. Cl.$^7$ .................................................. B67D 5/00
(52) U.S. Cl. ............................. 222/326; 222/82; 222/391
(58) Field of Search .............................. 222/82, 325, 326, 222/327, 386, 391

(56) References Cited

U.S. PATENT DOCUMENTS

| | | | |
|---|---|---|---|
| 4,131,217 | * 12/1978 | Sandegren | 222/326 |
| 4,681,524 | * 7/1987 | Ikeda et al. | 222/326 |
| 4,994,029 | * 2/1991 | Rohrbough | 222/82 |
| 5,192,008 | * 3/1993 | Hwan | 222/326 |
| 5,251,786 | * 10/1993 | Sarrine | 222/82 |
| 5,505,336 | * 4/1996 | Montgomery et al. | 222/326 |
| 5,709,668 | * 1/1998 | Wacks | 222/326 |

FOREIGN PATENT DOCUMENTS 641809  8/1928  (FR) .

* cited by examiner

Primary Examiner—Joseph A. Kaufman
(74) Attorney, Agent, or Firm—Dennison, Scheiner, Schultz & Wakeman

(57) ABSTRACT

A device for dispensing extrudable material, including a reservoir containing the extrudable material and having a dispensing orifice, a tubular endpiece communicating, in an in-use position, with the orifice of the reservoir, and being separable from the reservoir, a base including a reciprocally displaceable piston, a plate-forming element at the front end of the base and having a passage for receiving the endpiece, and a space for receiving the reservoir between the plate-forming element and the piston. A sealing piece having an orifice is disposed between the plate-forming element and the reservoir, the sealing piece having a sealing face facing towards the reservoir and shaped for receipt within the orifice. The tubular endpiece extends through the orifice of the sealing piece, and beyond the sealing piece at a proximal end. The sealing piece and the reservoir are constructed and arranged to mate with substantially friction-free thrust contact along a line of travel of the reservoir displaced towards the plate-forming element in response to the piston, to establish a sealed connection between the sealing piece and the reservoir and permit dispensing of the extrudable material through the orifice and the tubular endpiece; and to separate from each other under the effect of the reservoir being displaced away from the plate-forming element.

10 Claims, 3 Drawing Sheets

DEVICE FOR DISPENSING EXTRUDABLE MATERIAL, SUCH AS A PASTE FOR DENTAL USE

BACKGROUND OF THE INVENTION

The present invention relates to a device for dispensing an extrudable material.

A particular application of the invention lies in the field of dentistry, for dispensing pastes such as, for example, materials for making moldings, waxes for plugging purposes, composite resins or cements for tooth restoration treatments, or indeed insertion materials such as that described in French patent No. 89/07812, used to enlarge the gingival cleft.

More generally, the present invention can be used in other fields for extruding a variety of materials such as adhesives, cements, waxes, or elastomers.

The term "extrudable material" is used herein to designate any material which, unlike a liquid material, does not flow merely under the effect of gravity. Such materials can present a variety of viscosities. By way of example, the viscosity of the insertion material described in French patent No. 89/07812 to which the invention applies more particularly is between about 13,000 Pa.s and about 30,000Pa.s.

Numerous devices for dispensing extrudable material have been proposed in the state of the art, and in particular in the field of dentistry.

In general, such devices comprise a reservoir for containing said material to be extruded and for co-operating with piston-forming means that slide in said reservoir and that are suitable for enabling said material to be transferred into an endpiece extending said reservoir.

Two broad categories of dispenser device of the above type can be distinguished in the state of the art:
- those in which the reservoir and the endpiece are constituted by a single part; and
- those in which the reservoir and the endpiece are constituted by two distinct elements.

The present invention relates more particularly to a device belonging to the second category.

When designing a device belonging to said second category, the main problem that needs to be solved is naturally that of sealing between the endpiece and the reservoir, in particular during the stage in which the material is being delivered.

To solve this technical problem, presently-known devices make use of more or less elaborate mechanical fastenings between the endpiece and the reservoir, for example a screw fastening or a bayonet type fastening.

Such devices are described in particular in patents U.S. Pat. No. 3,121,516 and U.S. Pat. No. 3,767,085.

Although they provide a satisfactory solution to the problem of sealing between the endpiece and the reservoir, those known devices are often fragile, presenting a shape that is complex and easily clogged with the extruded substance, and difficult to clean. They are relatively awkward to use when changing the endpiece or the reservoir.

Also known in the state of the art, and in particular in the field of dentistry, are devices for injecting liquid, in particular hypodermically, said devices comprising a reservoir and a separable endpiece.

Such devices are described, for example, in documents BE 515,066, FR 2,245,382, FR 1,320,820, U.S. Pat. No. 1,818,670.

In those known devices, the reservoir containing the liquid to be injected is generally constituted by a glass bulb, and has an orifice which is closed by a plug, optionally a perforatable plug, which is made of an elastomeric material.

The plug has a central orifice in which said endpiece can be engaged as a force-fit with friction.

Sealing between the endpiece and the reservoir containing the liquid to be injected is consequently provided by co-operation between two cylindrical surfaces which are tightly pressed together by radial clamping, one of the surfaces also being elastically deformable.

In addition to be unsuitable for dispensing extrudable materials, those known devices suffer from the drawback of leading to the endpiece becoming mechanically secured to the reservoir, with the endpiece being separable from said reservoir only under the effect of an outside force that is relatively large.

Furthermore, since the reservoir is made of glass, it is particularly fragile and can under no circumstances be used for dispensing an extrudable material.

SUMMARY OF THE INVENTION

Under such conditions, an object of the present invention is to solve the technical problem consisting in providing a novel design of device for dispensing an extrudable material that guarantees a perfect sealing between the reservoir and the endpiece during the stage in which the material is being delivered, without requiring mechanical fastener means, and nevertheless enabling the reservoir and the endpiece to be separated very easily after said delivery stage.

Another object of the present invention is to solve this technical problem by providing a device which is easy to use and relatively moderate in price.

According to the present invention, the solution for solving this technical problem consists in a device for dispensing an extrudable material, the device comprising:
- a reservoir designed to contain the material and having at least one orifice;
- a separable tubular endpiece communicating, in its in-use position, with said reservoir via said orifice;
- a piston suitable, in use, for sliding inside said reservoir and for exerting sufficient force on said material to cause it to be delivered to the outside via the endpiece;
- a base carrying means for controlling the displacement of said piston and including a plate-forming element disposed in a plane that is substantially orthogonal to the displacement direction of said piston, said plate having a passage suitable for receiving said endpiece and being disposed facing the orifice of said reservoir;
- a sealing piece having an orifice extending the passage through said plate;
- means for making a sealed connection between said endpiece and said sealing piece, at least under the effect of said reservoir being displaced towards said plate; and
- means for preventing said sealing piece from moving relative to said plate, at least under the effect of the displacement of said reservoir towards said plate;
- the device being characterised in that said sealing piece has a sealing face facing towards said reservoir; said sealing face and the wall defining the orifice being suitable:
  - firstly for co-operating by substantially friction-free thrust contact, under the effect of said reservoir being displaced towards said plate in response to the displacement of said piston in said reservoir to establish a sealed connection; and secondly to be automatically separated from each other under the effect of said reservoir being displaced away from said plate.

Thus, the originality of the device of the present invention lies in the fact that the force developed by the piston for extruding the material serves to establish and maintain sealed contact between the separable endpiece and the reservoir. The greater this force, the greater the sealing. It therefore puts no limit on the viscosity of the material to be extruded.

In addition, because of the particular shape of the sealing face and of the reservoir orifice wall, the endpiece and said reservoir are automatically separated as soon as said faces are no longer held in contact with one pressing against the other.

Since the endpiece is separable from the reservoir, it is therefore extremely easy to change, insofar as there is no mechanical fastening and thus no unlocking operation required prior to removing the endpiece.

Unlike devices known in the state of the art, there is no radial clamping between the endpiece and the reservoir, with the thrust contact between the sealing face and the reservoir orifice wall having an axial component and not a component that is essentially radial.

In addition, contrary to devices known in the state of the art, the sealing in the device of the invention is achieved essentially along a line and not by mutual co-operation between two surfaces.

According to a particular characteristic of the device of the invention, said sealing piece is carried in peripheral and coaxial manner by said endpiece.

In a presently-preferred embodiment of the invention, the above-mentioned sealing piece has a substantially frusto-conical first face forming said sealing face and a substantially plane second face suitable for being thrust against said plate, thus forming the above-mentioned means for preventing said sealing piece from moving relative to said plate.

BRIEF DESCRIPTION OF THE DRAWINGS

The invention will be better understood and other objects, characteristics, and advantages thereof will appear more clearly on reading the following explanatory description made with reference to the accompanying drawings given solely in non-limiting manner, showing a presently-preferred embodiment of the invention, and in which:

FIG. 1 thus shows a device for dispensing an extrudable material in accordance with the present invention.

DESCRIPTION OF THE PREFERRED EMBODIMENTS

Figure 1:
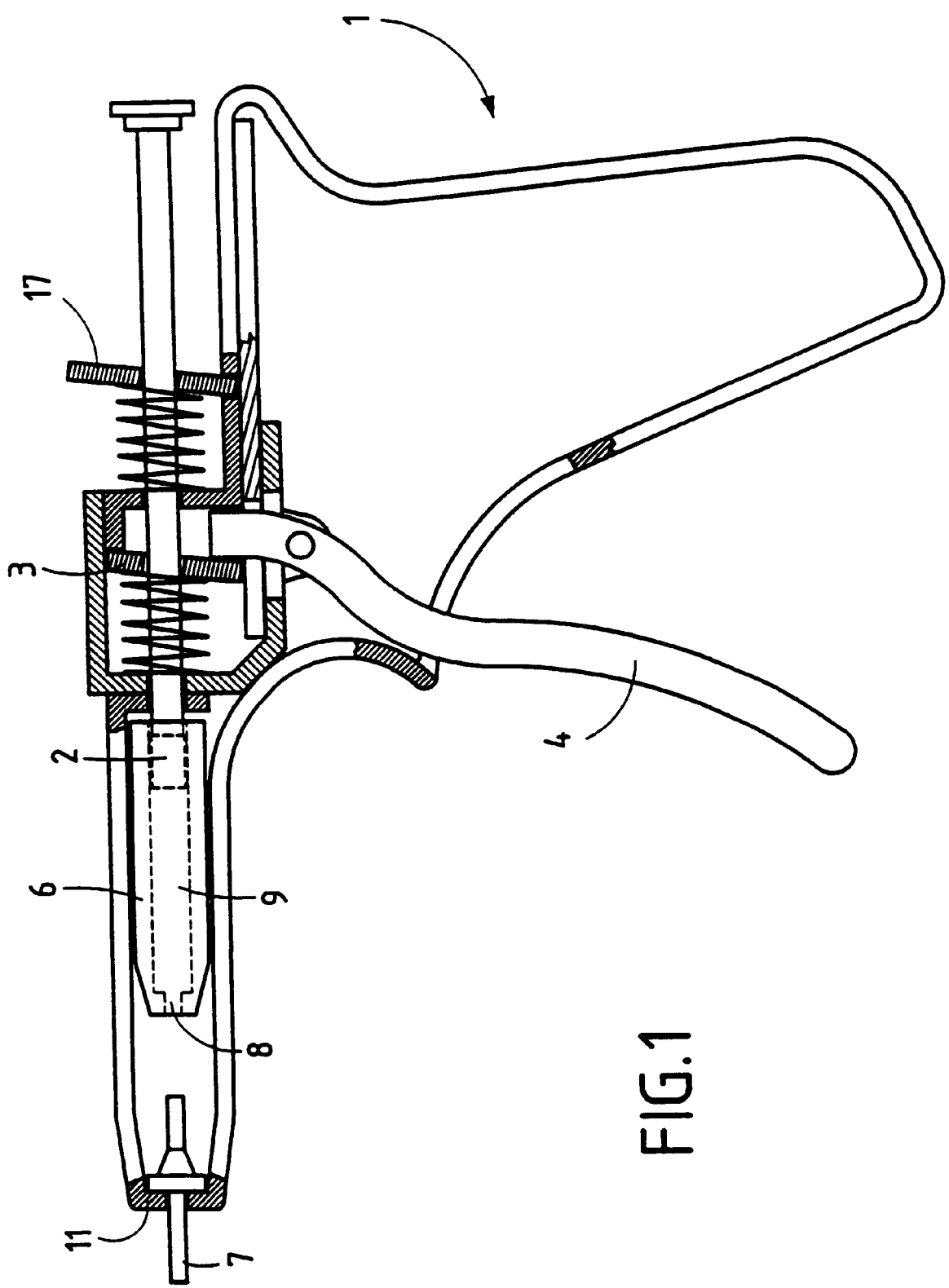
FIG. 1 is a cross-section of a device for dispensing extrudable material in accordance with the present invention, showing the endpiece and the reservoir at the beginning of their positioning stage.

The device comprises a base given overall reference numeral 1 and carrying means for controlling the displacement of a piston 2 whose rod is carried by said base.

These means for controlling piston displacement can be of various structures and in the example shown they comprise a plate-forming element 3 suitable for being actuated by a handle 4 shaped to transmit the force developed by the user between the fingers and the palm of the hand, with said force being multiplied by the lever effect.

The base 1 is designed, as explained below, to house a reservoir 6 designed to contain the material that is to be extruded and a separable endpiece 7 that is generally tubular in shape and that is disposed in line with the reservoir.

In its front portion (or mesial portion) the reservoir 6 has a face including an orifice 8 defined by a wall that is substantially cylindrical and opening out into a chamber 9 that is substantially cylindrical in shape containing the material to be extruded, which chamber is open via its face remote from its face that includes the orifice 8.

The piston 2 is adapted to slide in the chamber 9 of the reservoir 6 so as to exert sufficient force on the material to cause it to be delivered out through the orifice 8.

The base 1 is secured to a plate-forming element 11 disposed in a plane substantially orthogonal to the displacement direction of the piston 2, said plate having a through passage 12 suitable for receiving the endpiece 7 and disposed facing the orifice 8 of the reservoir.

In the example shown, the plate-forming element 11 is an integral portion of the base 1 and constitutes the front end thereof.

In general, a dispenser device of the present invention also has a sealing piece specifically shaped to connect the endpiece 7 to the reservoir 6 without fastening and in a manner that is sealed during the stage in which said material is being delivered.

To this end, the sealing piece generally has both an orifice extending the passage 12 in the plate 11, and a sealing face directed towards the reservoir 6 and suitable for co-operating with the orifice 8 in particular by bearing contact that is substantially without friction and without radial clamping, thus establishing sealing between itself and the wall of said orifice under the effect of the reservoir 6 being displaced towards the plate 11 in response to the piston 2 being displaced within the reservoir 6.

In addition, this sealing face is also shaped so as to separate automatically from the wall of the orifice 8 as soon as it is no longer held in contact therewith, i.e. under the effect of the reservoir being displaced in the direction away from the plate 11 in response to said piston being withdrawn.

Furthermore, the dispenser device of the invention generally has means for establishing a sealed bond between the endpiece 7 and the sealing piece and means for preventing said sealing piece moving relative to the plate 11, as described in greater detail below.

In a presently preferred embodiment of the invention, the sealing piece as given overall reference numeral 13 is carried in peripheral and coaxial manner by the endpiece 7.

The sealing piece 13 is generally fixed in permanent manner to the endpiece 7, e.g. by welding or adhesive, or indeed these two elements can constitute a single part as in the example shown.

Naturally, the sealing piece 13 can also be reversibly fastened to the endpiece 7, e.g. by screw means or as a tight fit.

In any event, it is appropriate to ensure that sealing between the endpiece 7 and the sealing piece 13 is perfect.

In an embodiment of the invention that is not shown, the above-mentioned sealing piece is an integral portion of the plate 11 and projects therefrom.

The sealing piece 13 can be disposed in such a manner that the proximal end 16 of the endpiece opens out inside the chamber 9 of the reservoir 6, as in the example shown.

Nevertheless, the general principle of the invention (FIG. 5) guarantees perfect sealing between the sealing piece 13 and the orifice 8, including when the proximal end of the endpiece does not open out into the chamber 9 of the reservoir 6.

Figure 5:
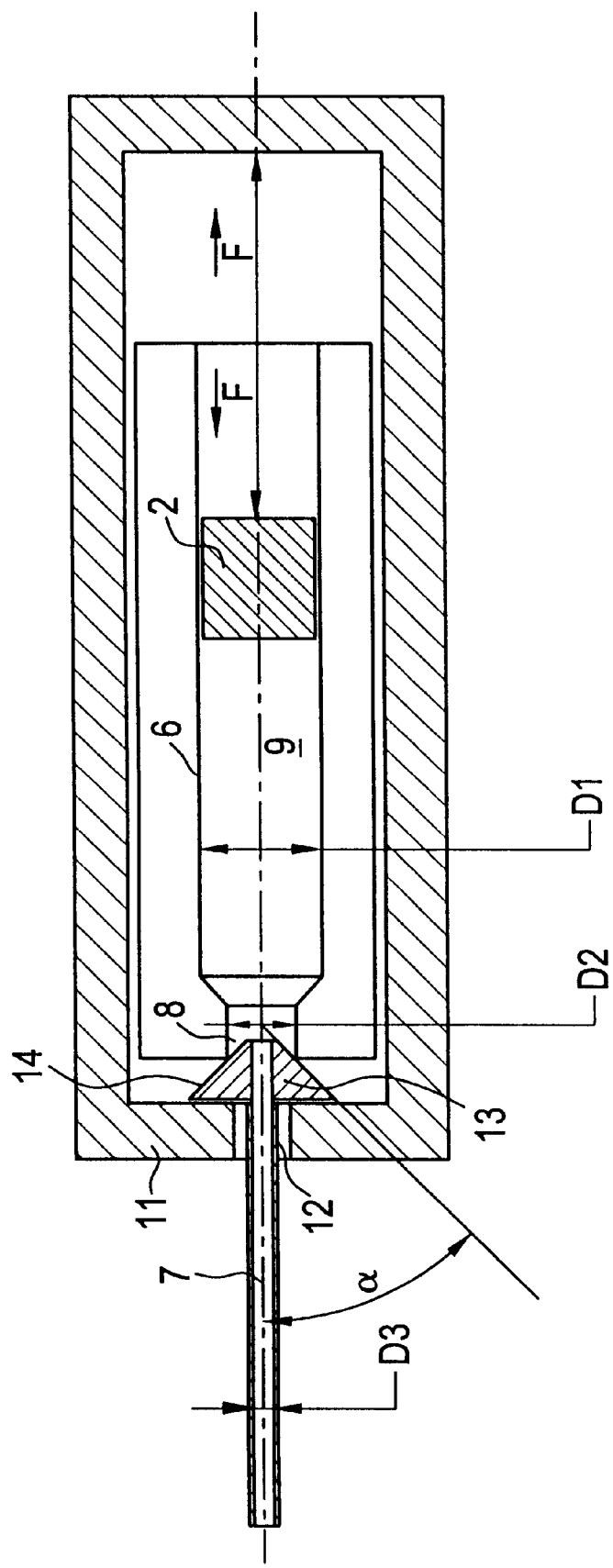
FIG. 5 is a view similar to FIG. 2 showing the principle on which the present invention is based.

Under such circumstances, the sealing piece 13 will be disposed at the end of the endpiece 7, as shown in FIG. 5.

According to a particular characteristic of the invention, the sealing piece 13 has a first face 14 of substantially frustoconical shape forming the above-mentioned sealing face, and a second face 15 that is substantially plane and remote from said first face for the purpose of coming into abutment against the plate 11 and preventing the sealing piece 13 from moving relative to the plate 11, at least under drive from displacement of the reservoir 6 towards the plate 11 in response to displacement of the piston 2 in the reservoir 6.

The first face 14 can also be substantially hemispherical in shape.

Advantageously, the wall defining the orifice 8 is substantially cylindrical.

In the invention it is important for the sealing face 14 and the wall defining the orifice 8 to come into contact with each other under the effect of the reservoir 6 being displaced towards the plate 11 along a line (intersection of a frustoconical or hemispherical surface and a cylindrical surface).

It will readily be understood that such contact takes place substantially without friction, and without radial clamping, unlike known devices in the state of the art.

According to another particular characteristic of the invention, the sealing face of the sealing piece and the wall defining the orifice 8 of the reservoir 6 are made of materials that are suitable for enabling relative deformation of the portions in contact, at least under the effect of the reservoir 6 being displaced towards the plate 11 in response to the piston 2 being displaced in the reservoir 6, thereby guaranteeing perfect sealing.

The selection of these materials depends essentially on the mechanical stresses which in turn depend directly on the viscosity of the substance.

By way of example, the sealing face of the sealing piece can be made of a plastics material such as polypropylene, for example, while the wall of the orifice 8 of the reservoir 6 can be made of metal.

The sealing face 14 and the wall of the orifice 8 can also both be made of a plastics material, such as polypropylene, for example.

The angle a defining the frustoconical surface of the sealing face 14 can vary over a wide range and, as will be understood, depends on the viscosity of the substance to be extruded.

In general, this angle will be between 5° and 85°, and will preferably be close to 20° for a substance whose viscosity is between 13,000 Pa.s and 30,000 Pa.s at 20° C.

The wall defining the orifice 8 of the reservoir 6 can be cylindrical, as described above, or it can have a chamfered edge.

In such circumstances, the angle forming the chamfered edge is advantageously different from the angle a defining the frustoconical surface of the sealing face 14 so that the contact between the sealing face 14 and the wall of the orifice 8 is established, as mentioned above, substantially along a line.

The diameter D1 of the chamber 9 of the reservoir 6, the diameter D2 of the orifice 8 of the reservoir 6, and the diameter D3 of the endpiece 7 are advantageously selected so as to ensure that the material to be extruded is properly dispensed without harming sealing. These diameters can easily be determined by the person skilled in the art.

In the presently-preferred embodiment of the invention, these diameters can be selected to have the following ratios:

D1 =2D2

3D3 =2D2

The way in which the device of the invention for dispensing an extrudable material is used is easily deduced from the structure of its component means as described above.

This operation is described below in greater detail with reference to FIGS. 2 to 4.

Figure 2:
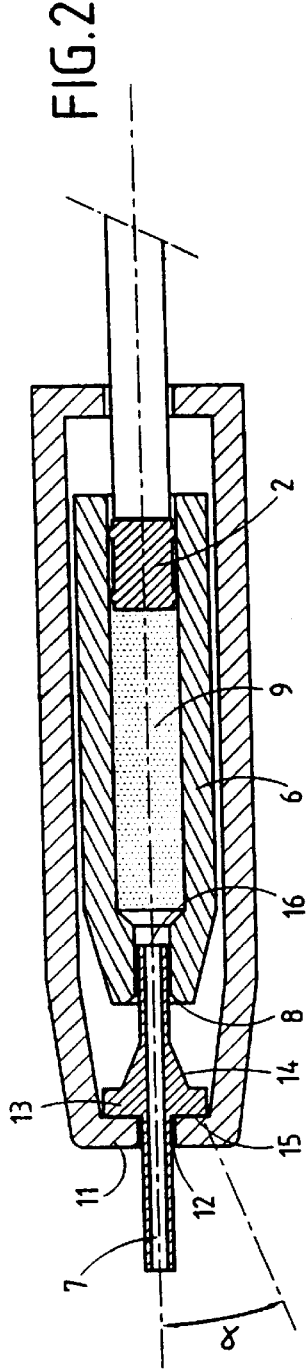
FIG. 2 is a cross-section view of the front portion of the device shown in FIG. 1, showing the endpiece and the reservoir at the end of their initial positioning stage.

In a first stage, shown in FIG. 2, the endpiece 7 and the reservoir 6 are positioned on the base 1.

To this end, the endpiece 7 is received in the passage 12 through the plate 11 and then the reservoir 6 is disposed in such a manner that the piston 2 penetrates into the chamber 9 and comes into contact with the material.

It should be observed that the piston 2 serves as means for supporting the reservoir 6.

Figure 3:
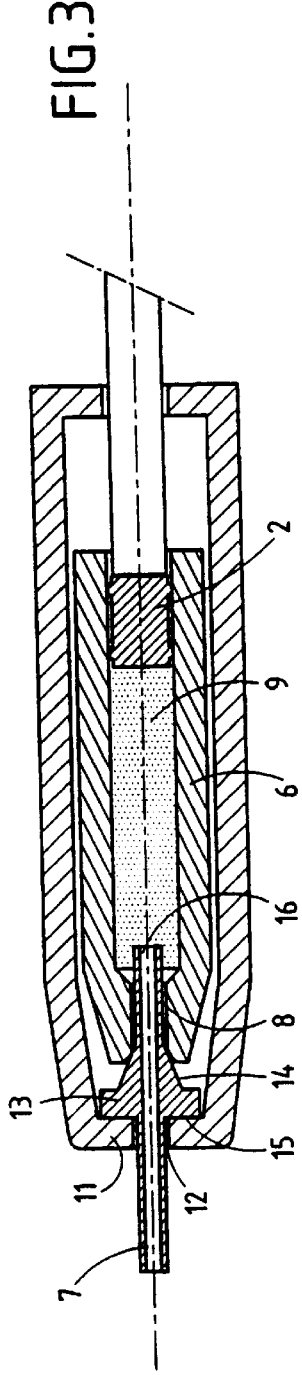
FIG. 3 is a view similar to FIG. 2, showing the endpiece and the reservoir during their approach and contact-making stage.

In a second stage shown in FIG. 3, the piston 2 is caused to be displaced towards the plate 11 by means of the handle 4, thereby causing the reservoir 6 to approach the endpiece 7 and then to come into contact therewith, as will readily be understood.

At the end of this stage, the sealing face 14 of the sealing piece 13 comes into contact with the wall defining the orifice 8 of the reservoir 6.

Figure 4:
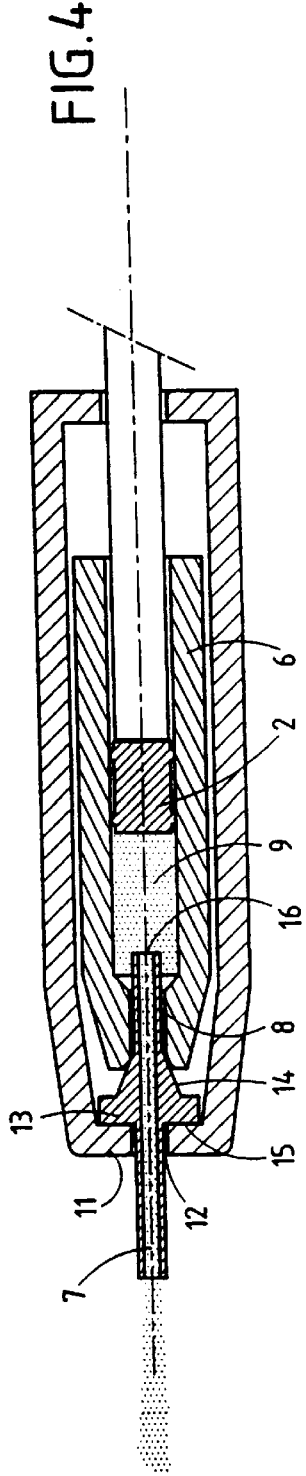
FIG. 4 is a view similar to FIGS. 2 and 3 showing the endpiece and the reservoir during the stage of delivering the material.

In a third stage as shown in FIG. 4, the material is delivered to the outside via the endpiece 7.

The force exerted by the piston 2 on the material to be extruded guarantees sealing between the surface 14 of the sealing piece 13 and the orifice 8.

As will readily be understood (see also FIG. 5), the plate 11 exerts a reaction force against the force from the piston, thereby enabling the endpiece 7 to be coupled to the reservoir 6 without fastening, and to do so in a manner that is sealed, at least during the stage in which the material is delivered.

Whatever the force exerted by the piston on the material to be extruded, sealing is guaranteed, with sealing becoming stronger as the force exerted by the piston increases.

To avoid the piston being withdrawn during the stage in which material is being delivered, the base 1 is preferably provided with non-return means, for example in the form of an inclined plate 17 (FIG. 1) which in use co-operates with a spring and has an orifice enabling the piston rod to move freely while the plate is held in an upright position (i.e. while said plate is substantially orthogonal to the piston rod) and preventing the piston 2 from moving in the direction opposite to displacement towards the plate 11 while the plate 17 is in its inclined position.

The endpiece 7 can be withdrawn in relatively easy manner.

To this end, the inclined plate 17 is stood up so as to allow the piston to be moved towards the proximal portion of the base. During this stage, the endpiece 7 can easily be separated from the reservoir 6 and withdrawn from the passage 12 through the plate 11 (once there is no force holding the sealing face 14 in contact with the wall of the orifice 8 of the reservoir 6, separation is easy).

The above-described device for dispensing an extrudable material presents numerous advantages.

Firstly, it makes it easy to install and to change the endpiece and/or the reservoir while nevertheless guaranteeing perfect sealing.

In the field of dentistry, it is thus possible to make use of a plurality of endpieces of different diameters using the same reservoir for different indications, which is impossible with devices known in the state of the art since they require the endpiece to be engaged as a force-fit in the plug, and thus require the said endpiece to be of a predetermined size.

Because of the absence of any mechanical fastening between the endpiece and the reservoir they can be manufactured without problems of tolerance.

The base can easily be cleaned and sterilized prior to treatment. The endpiece and the sealing piece can advantageously be for single use only.

Finally, the device is of relatively moderate cost.

What is claimed is:

1. A device for dispensing an extrudable material comprising:

a reservoir constructed and arranged to contain the extrudable material and having at least one dispensing orifice at a first end thereof;

a tubular endpiece constructed and arranged to communicate, in an in-use position, with the orifice of said reservoir, and being separable from said reservoir;

a base comprising a piston, means for controlling reciprocal displacement of the piston in a direction between a rearward position and a forward position towards a front end of the base, a plate-forming element disposed at the front end of the base in a plane that is substantially orthogonal to the displacement direction of said piston, said plate-forming element having a passage constructed and arranged for receiving said endpiece, and means for receiving the reservoir between the plate-forming element and the rearward position of the piston with the orifice disposed facing the plate-forming element, the means for controlling being constructed and arranged to exert sufficient force on an opposite end of the reservoir to cause the extrudable material to be dispensed through the orifice;

a sealing piece having an orifice and disposed between said plate-forming element and said reservoir, the sealing piece having a sealing face facing towards said reservoir and shaped for receipt within the orifice, the tubular endpiece extending into the orifice of the sealing piece from a distal end of the sealing piece, with the orifice of the sealing piece extending the tubular endpiece at a proximal end of the sealing piece;

means for making a sealed connection between said endpiece and said sealing piece, at least under the effect of said reservoir being displaced by the piston towards said plate-forming element; and means for preventing said sealing piece from moving relative to said plate-forming element, at least under the effect of the displacement of said reservoir by the piston towards said plate-forming element;

wherein the sealing piece and the reservoir are constructed and arranged:

to mate with substantially friction-free thrust contact, substantially along a line of travel of said reservoir displaced towards said plate-forming element in response to the displacement of said piston, to establish a sealed connection between the sealing piece and the reservoir and permit dispensing of the extrudable material through the orifice and the tubular endpiece; and to separate from each other under the effect of said reservoir being displaced away from said plate-forming element upon retraction of the piston.

2. The device according to claim 1, wherein the sealing face and the orifice are shaped to cooperate by thrust contact substantially along a line.

3. The device according to claim 1, wherein said sealing piece is carried in peripheral and coaxial manner by said endpiece.

4. The device according to claim 1, wherein the sealing piece has a substantially frustoconical first face forming said sealing face and a substantially planar second face constructed and arranged to be thrust against said plate-forming element, thus forming the means for preventing said sealing piece from moving relative to said plate.

5. The device according to claim 1, wherein the sealing face of the sealing piece and the orifice are made of a material adapted for relative deformation of surfaces that come into contact, at least under the effect of displacement of the reservoir towards the plate-forming element in response to the displacement of the piston.

6. The device according to claim 5, wherein the sealing face is made of a plastic material.

7. The device according to claim 6, wherein the orifice is made of metal or of a plastic material.

8. The device according to any claim 1, wherein the orifice of the reservoir forms a chamfered edge.

9. The device according to claim 1, wherein the base (1) includes means to prevent the piston being displaced in a direction opposite to its displacement direction towards the plate.

10. The device according to claim 1, wherein the sealing piece is disposed in such a manner that the proximal end of the endpiece opens into the reservoir in an in-use position.

* * * * *